United States Patent [19]

Koch

[11] 4,408,068

[45] Oct. 4, 1983

[54] PROCESS FOR THE PREPARATION OF OPTICALLY ACTIVE 2-CHLOROPROPIONIC ACID ESTERS

[75] Inventor: Manfred Koch, Eppstein, Fed. Rep. of Germany

[73] Assignee: Hoechst Aktiengesellschaft, Frankfurt am Main, Fed. Rep. of Germany

[21] Appl. No.: 342,584

[22] Filed: Jan. 25, 1982

[30] Foreign Application Priority Data

Jan. 27, 1981 [DE] Fed. Rep. of Germany ....... 3102516

[51] Int. Cl.$^3$ ............................................... C07C 69/63
[52] U.S. Cl. ................................................... 560/226
[58] Field of Search ........................................ 560/226

[56] References Cited

U.S. PATENT DOCUMENTS 4,334,083 6/1982 Buathier et al. ................... 560/226

OTHER PUBLICATIONS

Darzens, M. G. *Comptes Rendus*, vol. 152 (1911) pp. 1314–1317 and 1601–1603.
Frankland, Percy Faraday et al. *J. of the Chemical Society*, vol. 105, (1914) pp. 1101–1116.

Primary Examiner—Natalie Trousof
Assistant Examiner—L. Hendriksen
Attorney, Agent, or Firm—Curtis, Morris & Safford

[57] ABSTRACT

What is disclosed is a process for the preparation of optically active 2-chloropropionic acid esters by the decomposition of optically active 2-chlorosulfinoxypropionic acid esters in the presence of quaternary ammonium or phosphonium salts as catalysts.

8 Claims, No Drawings

PROCESS FOR THE PREPARATION OF OPTICALLY ACTIVE 2-CHLOROPROPIONIC ACID ESTERS

The present invention relates to a process for the preparation of optically active 2-chloropropionic acid esters by the decomposition of optically active 2-chlorosulfinoxypropionic acid esters in the presence of catalysts.

It is known that alcohols and hydroxycarboxylic acids can be converted to the corresponding chlorine compounds by reaction with molar amounts of pyridine and thionyl chloride (Darzens, C.r. 152 (1911), pp. 1314 and 1601). The reaction proceeds according to the following scheme:

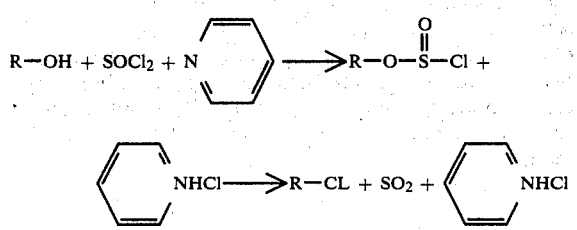

According to this process, Niemann et al. (J. org. Chem. 8, (1943), p. 401), starting from racemic lactic acid methyl ester, obtained 2-chloro-propionic acid methyl ester with a yield of 71% of theory, and likewise Gerrard et al. (J. Chem. Soc. 1937 I, p. 153), starting from D-lactic acid ethyl ester obtained a 70% yield of L-2-chloropropionic acid ethyl ester having a specific rotation of $[\alpha]_D^{17} = -18.1°(\alpha_{589}^{17} = -19.56°)$, corresponding to an optical purity of about 90%.

Because of the poor yield and the insufficient optical purity of the 2-chloropropionic acid esters so obtained, this process is unfit for the industrial manufacture of 2-chloropropionic acid esters of a high optical purity. Furthermore, the large amount of base in the reaction product, which must be recovered in complicated operations is disadvantageous.

It is furthermore known that the decomposition of the chlorosulfinic acid ester formed as an intermediate according to the above scheme can be obtained with the use of catalytic amounts of base (0.1 mol per mol of hydroxy component or thionyl chloride; Houben-Weyl, vol. VI/2, p. 435).

Thus, Liebermann (Nature 160 (1947), p.903) and Gerrard (Nature 159 (1947), p. 263) obtained 2-chloro-propionic acid ethyl ester with a yield of about 95% of theory in the reaction of racemic lactic acid ethyl ester and thionyl chloride with the addition of a catalytic amount of pyridine. In this method the 2-chloropropionic acid ester formed can be directly distilled off from the reaction mixture. Because of the high yield and the simple operational technology, which moreover prevents pollution, this process offers numerous advantages as compared to the reaction with molar amounts of base.

In trying to adapt this process, described solely as applicable to the production of racemic 2-chloropropionic acid ethyl ester, to the production of optically active 2-chloropropionic acid esters starting from optically active D- or L-lactic acid esters, it has been observed that the good chemical yield is maintained but the optical activity is lost to a substantial extent. The 2-chloropropionic acid methyl ester obtained according to the process of Liebermann by reaction of L-lactic acid methyl ester, thionyl chloride and catalytic amounts of pyridine had an optical activity of about 55% of theory only, that is, the loss of optical activity amounts to more than 40% of theory. Therefore, this method is not suitable for the preparation of optically active 2-chloropropionic acid esters.

Surprisingly, it has now been observed that the use of phase transfer catalysts permits the conversion of optically active D- and L-lactic acid esters to the corresponding L- or D-chloro-propionic acid esters with high chemical yield (92 to 96% of theory) and high optical purity (95 to 98% of theory).

A feature of the invention is therefore a process for the preparation of optically active 2-chloropropionic acid esters of the formula I

in which R is a $(C_1-C_6)$alkyl radical, by the decomposition of optically active 2-chlorosulfinoxypropionic acid esters of the formula II

in which R is as defined for formula I, in the presence of catalysts, which comprises using onium salts (quaternary ammonium or phosphonium salts) as catalysts.

The optically active 2-chloropropionic acid esters I prepared according to the invention are interesting intermediates for the manufacture of optically active hormone type herbicides or herbicidal phenoxyphenoxypropionic acid derivatives.

In the process of the invention, D- or L-chlorosulfinoxypropionic acid esters of the formula II are continuously metered into a heated and evacuated reactor vessel provided with a decomposition catalyst, while the D- or L-chloropropionic acid ester is simultaneously distilled off together with sulfur dioxide. The optically active 2-chloropropionic acid ester is collected in a cooled receiver, and sulfur dioxide is condensed in a further receiver or absorbed in an aqueous lye.

The reactor vessel is heated to 60°-140° C., preferably 180° to 120° C., and the reduced pressure is from 10 to 150, preferably 20 to 80, mm Hg. Temperature and reduced pressure are adjusted in such a manner that the D- or L-2-chloropropionic acid ester distils off immediately from the reactor.

As decomposition catalysts, quaternary ammonium or phosphonium salts (onium salts), preferably chlorides, are used. Examples thereof are benzyltributylammonium chloride, benzyltriethylammonium chloride, tetraethylammonium chloride, tetrabutylammonium chloride, di-$(C_{16}-C_{18})$-alkyl-dimethylammonium chloride, tri-$(C_{16}-C_{18})$-alkyl-methylammonium chloride, methyltri-$C_8-C_{10}$-alkyl-ammonium chloride, trimethyl-phenyl-ammonium chloride, dimethylpiperidinium chloride, N-benzyl-N-methylephedrinium chloride, N-dodecyl-N-methylephedrinium chloride, tetrabutylphosphonium chloride, tetraoctylphosphonium chloride, hexadecyltributylphosphonium chloride, N-dodecylthiazolium chloride, N-methyl-pyridinium chloride, N-dodecylpyridinium chloride, trioctylpropylammonium chloride.

The required amount of catalyst is extremely small, that is, from $1.10^{-4}$ to $5.10^{-3}$ mols per mol of chlorosulfinoxypropionic acid ester.

The chlorosulfinoxypropionic acid ester of the formula II used for the reaction is obtained according to known methods, for example reaction of D- or L-lactic acid esters with thionyl chloride (Houben-Weyl, vol.-VI/2, p. 431), and can be used for the decomposition reaction in unpurified state.

In the case where an excess of thionyl chloride has been used for preparing II, the excess distills off from the reaction vessel together with the 2-chloropropionic acid ester.

The optically active 2-chloropropionic acid ester condensed in the receiver contains small amounts of dissolved sulfur dioxide and possibly small amounts of thionyl chloride, and it can be purified by a rectifying distillation.

The yield of optically active 2-chloropropionic acid ester is from 95 to 98% of theory, relative to the optically active 2-chlorosulfinoxypropionic acid ester, or from 92 to 96% of theory, relative to the optically active lactic acid ester. When using optically active lactic acid ester, the optical purity of the 2-chloropropionic acid ester obtained is from 95 to 98% of theory.

The reaction proceeds with nearly quantitative conversion of configuration. Thus, an L-2-chloropropionic acid ester is formed from a D-2-sulfinoxypropionic acid ester, and an L-2-sulfinoxypropionic acid ester gives a D-2-chloropropionic acid ester.

The following examples illustrate the invention.

(1) Preparation of 2-chlorosulfinoxypropionic acid ester (Starting material, general method) 1.0 mol of L- or D-lactic acid ester is added dropwise at room temperature and with agitation to 1.05 mols of thionyl chloride. After the hydrogen chloride development has come to an end, the clear solution is left standing for 24 hours at room temperature. The crude L- or D-2-chloro-sulfinoxypropionic acid ester is used for the process of the invention without further purification.

If desired, purification can be carried out by distillation. In the case of L-lactic acid methyl ester, 181 g=97% of theory of L-2-chlorosulfinoxypropionic acid methyl ester having a boiling point of 45° C./0.013 mbar and a refractive index $n_D^{21.5}=1.4646$ are obtained after distillation.

(2) EXAMPLES according to the process of the invention

General indications

The apparatus used for the decomposition of the 2-chlorosulfinoxypropionic acid ester consisted of a 100 ml two-necked flask provided with a dropping funnel (for dosing the 2-chlorosulfinoxypropionic acid ester), a Liebig condenser cooled with an ice/sodium chloride mixture and connected to the flask via a short Vigreux column; furthermore two receivers cooled with ice/sodium chloride (for collecting the 2-chloropropionic acid ester formed) and a further receiver cooled to −78° C. for condensing sulfur dioxide, which receivers were connected to the Liebig condenser. The apparatus was evacuated by means of a water jet vacuum, and the reactor vessel was heated in an oil bath.

2.1 L-2-chloropropionic acid methyl ester 474 g of crude D-2-chlorosulfinoxypropionic acid methyl ester (prepared by reaction of 2.4 mols of D-lactic acid methyl ester, $[\alpha]_D^{23}=8.03°$, and 2.56 mols of thionyl chloride, according to Example (1) were dosed within 2 hours into the reactor vessel containing 0.75 g of tri-($C_6$–$C_8$alkyl)-methylammonium chloride and heated to 100° C. Dosage was carried out in such a manner that a reduced pressure of about 40 to 60 mm Hg was maintained and the L-2-chloropropionic acid methyl ester which formed (head temperature about 50° C., 50 mm) distilled off. The dosage being complete, the contents of receivers 1 and 2 were combined. 306 g of crude L-2-chloropropionic acid methyl ester were obtained, 1.7 g remained in the reactor. On rectification of the crude L-2-chloropropionic acid methyl ester for separating sulfur dioxide and small amounts of thionyl chloride, 279 g=95% of th. (relative to D-lactic acid methyl ester) of pure L-2-chloropropionic acid methyl ester having a boiling point of 42° C./36 mbar and a specific rotation of $[\alpha]_D^{20}=-25.6°$ (1,1.0) were obtained.

(2.2) L-2-chloropropionic acid methyl ester

In analogy to 2.1, but with 0.3 g of methyltri($C_6$–$C_8$-alkyl)-ammonium chloride, there were obtained:
276 g=93.9% of th. of L-2-chloropropionic acid methyl ester having a specific rotation of $[\alpha]_D^{20}=-25.4°$ (1, 1.0).

(2.3) L-2-chloropropionic acid methyl ester

In analogy to 2.1, but with 0.5 g of triethylbenzylammonium chloride, there were obtained:
280.6 g=95.5% of th. of L-2-chloropropionic acid methyl ester having a specific rotation of $[\alpha]_D^{22}=-25.7°$ (1, 1.0).

(2.4) L-2-chloropropionic acid methyl ester

In analogy to 2.1 but with 0.5 g tetraoctylphosphonium chloride, there were obtained:
278 g=94.7% of th. of L-2-chloropropionic acid methyl ester having a specific rotation of $[\alpha]_D^{22}=-25.3°$ (1, 1.0).

(2.5) D-2-chloropropionic acid methyl ester

In analogous manner, but starting from L-lactic acid methyl ester ($[\alpha]_D^{25}=-8.56°$) and with the use of 0.5 g of tri-($C_8$–$C_{10}$-alkyl)-methylammonium chloride, there were obtained:
276.3 g=94% of th. of D-2-chloropropionic acid methyl ester having a specific rotation $[\alpha]_D^{22}=+26.3°$ (1, 1.0).

(2.6) D-2-chloropropionic acid ethyl ester

In analogous manner, but starting from commercial redistilled L-lactic acid ethyl ester ($[\alpha]_D^{24}=-10.6°$ (1, 1.0) and with the use of 0.75 g of tri($C_6$–$C_8$-alkyl)-methylammonium chloride, there were obtained: 306 g=93.3% of th. of D-2-chloropropionic acid ethyl ester, having a specific rotation of $[\alpha]_D^{20}=+19.1°$.

(Comparative Tests)

(1) D-2-chloropropionic acid methyl ester (according to Liebermann, Nature, Vol. 160 (1947),p.903).

0.5 Mol of thionyl chloride (59.5 g) was added dropwise at room temperature (exterior ice cooling) to 1.0 mol of L-lactic acid methyl ester (104 g, $[\alpha]_D^{21.5} = -8.44°$ (1, 1.0) while passing a light $N_2$ current through the reactor. After the development of hydrogen chloride had come to an end, a further 0.6 mol of thionyl chloride (71.5 g) were added, and the solution was left for 24 hours at room temperature. After addition of 1 ml of pyridine, the batch was heated for 3 hours in a water bath at about 95°–100° C., subsequently D-2-chloropropionic acid ester was distilled off via a column in a water jet vacuum. 106 g=86.5% of D-2-chloropropionic acid methyl ester having a specific rotation of $[\alpha]_D^{22} = +15.3°$ (1, 1.0).

(2) L-2-Chloropropionic acid methyl ester (according to Gerrard, Kenyon, Phillips (J.Chem.Soc. 1937 I, p.153)

0.398 Mol of D-lactic acid methyl ester (41.4 g $[\alpha]_D^{23} = 8.03°$ (1, 1.0)) and 0.405 mol of pyridine (32 g) were introduced into a 250 ml four-necked flask, and 0.405 g mol of thionyl chloride (48 g) was added within 45 minutes at an inner temperature of 20°–30° C. On adding the thionyl chloride dropwise, a viscous paste of pyridine hydrochloride was formed, so that the batch could not be stirred any longer after addition of about two thirds of the thionyl chloride. The addition being complete, the batch was heated for 1 hour at 60° C., cooled, and the reaction mixture was poured onto icewater. Subsequently, it was extracted twice with a total of 400 ml of diethyl ether. Diethyl ester was distilled off via a column under normal pressure, and the L-2-chloropropionic acid methyl ester was distilled off in a water jet vacuum, boiling point 38° C., pressure 21 mm Hg. 35.6 g=72.8% of L-2-chloropropionic acid methyl ester having a specific rotation of $[\alpha]_D^{26} = -23.5°$ (1, 1.0) were obtained.

What is claimed is:

1. A method for making an optically active 2-chloropropionic acid ester of the formula

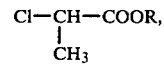

wherein R is $(C_1-C_6)$ alkyl, which method comprises decomposing an optically active 2-chlorosulfinoxypropionic acid ester of the formula

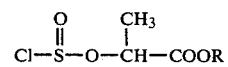

in the presence of a quaternary ammonium salt or of a phosphonium salt as a catalyst.

2. A method as in claim 1 wherein said catalyst is a quaternary ammonium salt.

3. A method as in claim 2 wherein said salt is a chloride.

4. A method as in claim 1 wherein said catalyst is a phosphonium salt.

5. A method as in claim 4 wherein said salt is a chloride.

6. A method as in claim 1 wherein said catalyst is present in an amount of $1(10^{-4})$ to $5(10^{-3})$ mol per mol of said 2-chlorosulfinoxypropionic acid ester.

7. A method as in claim 1 wherein said decomposition is performed at a temperature from 60° C. to 120° C.

8. A method as in claim 7 wherein said 2-chloropropionic acid ester is distilled off from the reaction mixture under reduced pressure concurrently with said decomposition.

* * * * *